US006244213B1

(12) United States Patent
Tedders et al.

(10) Patent No.: US 6,244,213 B1
(45) Date of Patent: Jun. 12, 2001

(54) DEVICE AND METHOD FOR RAPIDLY LOADING INSECT EGGS INTO REARING CONTAINERS

(75) Inventors: Walker L. Tedders; John L. Blythe, both of Perry, GA (US)

(73) Assignee: The United States of America as represented by the Secretary of the Agriculture, Washington, DC (US)

( * ) Notice: Subject to any disclaimer, the term of this patent is extended or adjusted under 35 U.S.C. 154(b) by 0 days.

(21) Appl. No.: 09/489,622

(22) Filed: Jan. 24, 2000

(51) Int. Cl.[7] .................................................. A01K 29/00
(52) U.S. Cl. ............................................................ 119/6.6
(58) Field of Search ...................................... 119/6.5, 6.6

(56) References Cited

U.S. PATENT DOCUMENTS

| | | | |
|---|---|---|---|
| 2,539,633 | * | 1/1951 | Morrill ................................... 119/6.5 |
| 3,399,653 | * | 9/1968 | Tiner et al. ............................ 119/6.5 |
| 4,106,438 | * | 8/1978 | Nelson ................................... 119/6.5 |
| 4,765,274 | * | 8/1988 | Pizzol et al. ........................... 119/6.5 |
| 4,850,305 | * | 7/1989 | Georgi et al. ......................... 119/6.5 |
| 5,178,094 | * | 1/1993 | Carr et al. ............................. 119/6.5 |
| 5,351,643 | * | 10/1994 | Hughes ................................. 119/6.5 |
| 5,784,991 | * | 7/1998 | Ukishiro et al. ...................... 119/6.5 |
| 5,819,685 | * | 10/1998 | Kappelt et al. ....................... 119/6.5 |

* cited by examiner

Primary Examiner—Thomas Price
(74) Attorney, Agent, or Firm—M. Howard Silverstein; John D. Fado; G. Byron Stover

(57) ABSTRACT

A method and apparatus for rapidly loading small particulate matter such as insect (e.g., lacewing) eggs into containers for uniformly distributing the eggs into individual units of the containers. The apparatus uses a fluid dispensing system to move the eggs from a holder to the containers located below. The method of the present invention provides a volumetrically measured quantity of eggs to be distributed to the individual units of the containers.

6 Claims, 4 Drawing Sheets

DEVICE AND METHOD FOR RAPIDLY LOADING INSECT EGGS INTO REARING CONTAINERS

BACKGROUND OF THE INVENTION

The practice of using insects (e.g., lacewings) in reducing the use of chemical insecticides in agriculture, especially on edible vegetation, has gained in popularity. Presently, the high cost of insects such as adult lacewings has been prohibitive for commercial growers since large quantities are needed for practical use. Up until now, packaging lacewing eggs has proved to be tedious and labor intensive. Currently, commercial rearers of lacewings have been manually loading lacewing eggs into rearing units. The rearing units are made up of individual cells, with each unit having 500 cells. This method of manually loading includes first placing a weighed quantity of eggs (which are small particulate-like matter the size of salt grains) in a common salt shaker and shaking the eggs into the unit so that at least one egg enters a cell. Food is placed into the cells by a similar method. Generally two or three eggs enter a cell to ensure that at least one viable lacewing egg is present in each cell of the rearing unit. Once the eggs are placed within the cells, the rearing unit is closed by gluing a sheet of polyester fabric over the top. Each cell in the unit will then produce only one lacewing adult since the larvae are cannibalistic. Placing the eggs requires approximately 60 seconds per rearing unit. This method is very labor intensive, which is one of the major problems with commercial lacewing production.

SUMMARY OF THE INVENTION

The present invention removes the need of manual placement of insect eggs into the rearing units. The invention is a device which rapidly loads and distributes insect (e.g., lacewing) eggs and their food supply into vertical rearing units. The device automatically dispenses a measured quantity of eggs and food into each of the cells with speed and accuracy. In the present invention the loading process fills the rearing containers at a rate of 5 sec for every 500 cells.

DETAILED DESCRIPTION OF THE INVENTION

Figure 1:
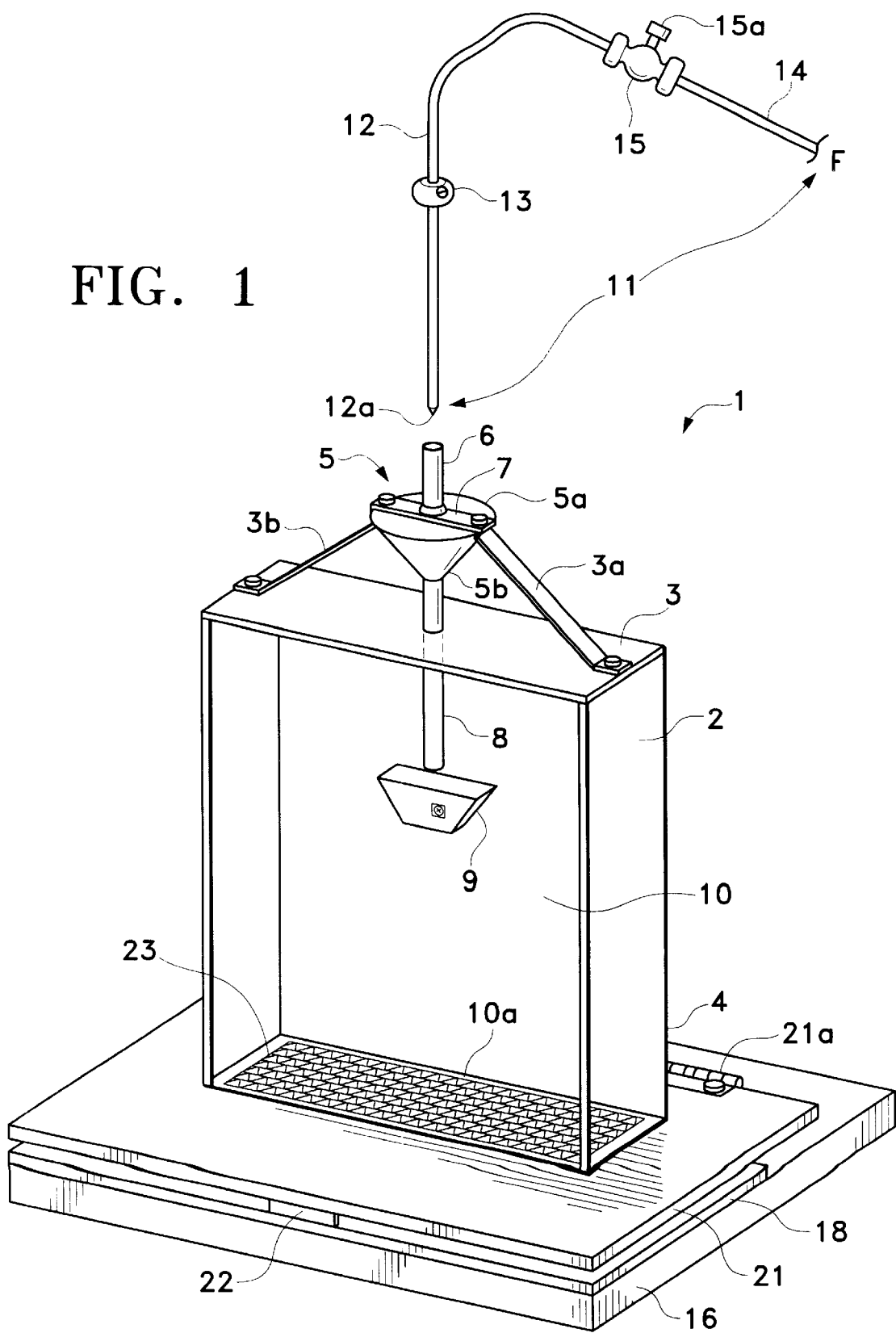
FIG. 1 shows the device of the present invention with the rearing unit in position.

The present invention eliminates the need for manually placing insect (e.g., lacewing) eggs into individual cells of a rearing unit. As shown in FIG. 1, the device 1 includes a frame 2 having a top portion 3 and a bottom portion 4; the frame 2 may be made of any smooth surface transparent material (e.g., plexiglass) having the characteristics described herein, for example the frame 2 may be a clear plastic box. The top portion 3 houses brackets 3a and 3b which secures a funnel 5 to the frame 2. The funnel 5 has a wider top end 5a and a narrow, apertured bottom end 5b. The top end 5a houses a tube guide 6 which is attached to the top end 5a of the funnel 5 through a support bracket 7. A drop tube 8 is attached to the bottom end 5b of the funnel 5 and extends to a height directly above and centrally positioned with respect to a reservoir 9 which may be conical (or any other shape capable of holding insect eggs and food supply). Preferably, the shape of the top of the reservoir 9 is the same as the top portion 3, that is both are rectangular, though the dimensions (i.e., length and width) of the top of the reservoir 9 are smaller than the top portion 3; additionally the shape of the bottom of the reservoir 9 is the same as the top, though smaller. Mounting brackets 3c and 3d (shown in FIG. 4) attach the reservoir 9 to the frame 2. A distribution chamber 10 having a chamber opening 10a (shown here with rearing unit 23), positioned below the reservoir 9, distributes the food and eggs below, as will be described hereinbelow. The reservoir 9 is located in the center of the distribution chamber 10; preferably the top edge of the reservoir 9 is about 16.5 cm below the top portion 3.

A fluid delivery system 11 delivers pressurized fluid, preferably air, to the top of reservoir 9 as will be described hereinbelow. The fluid delivery system 11 includes an insert tube 12 having a tip 12a and a stop 13. The stop 13 allows the insert tube 12 to vertically move in and out through the funnel 5 via the tube guide 6, through drop tube 8 to a position above the reservoir 9. The upper portion of the insert tube 12 is attached to a fluid (e.g., air) source 14 through a valve (e.g., push-button) 15.

Figure 2:
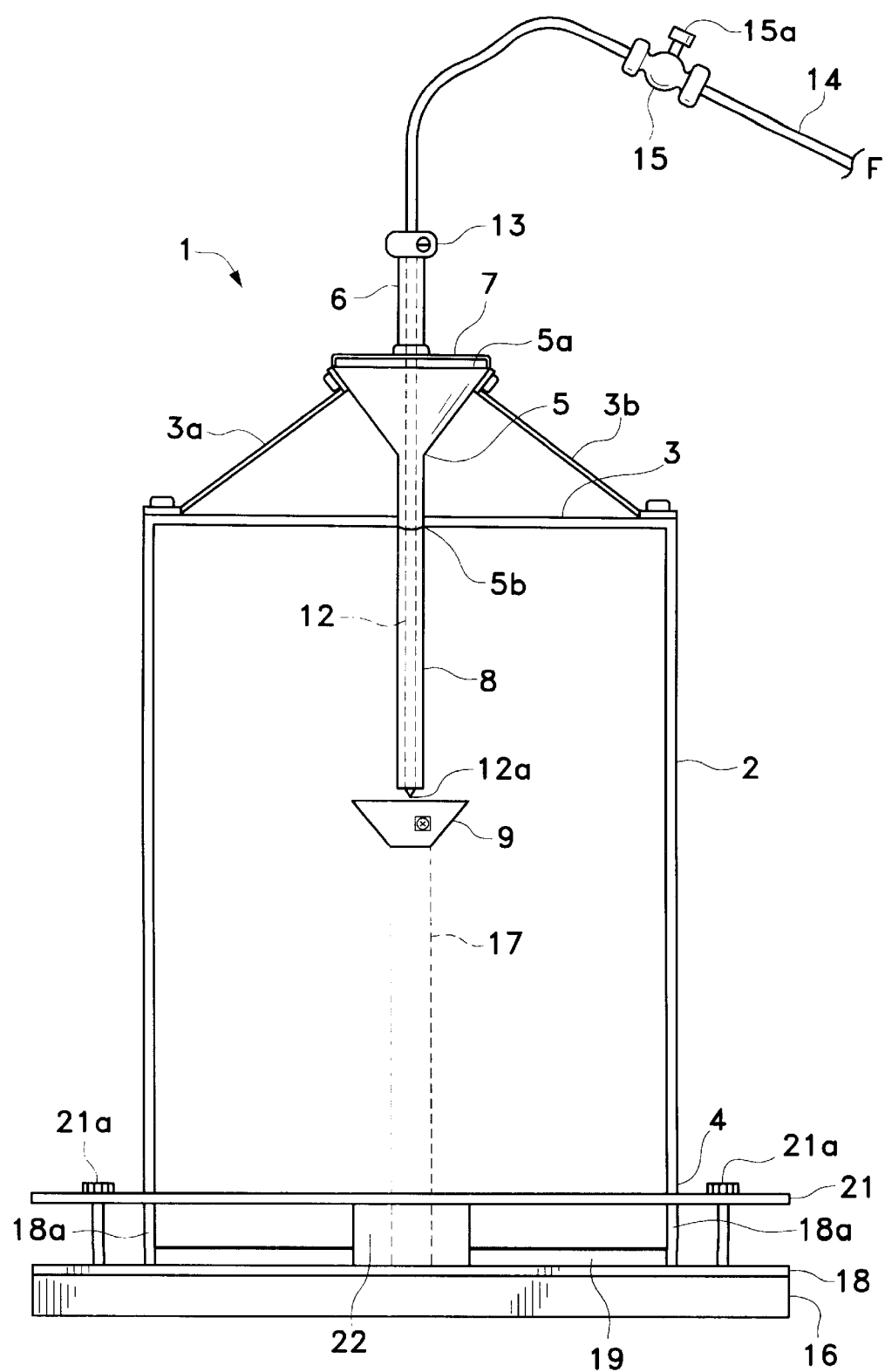
FIG. 2 shows the front view of the device.
Figure 4:
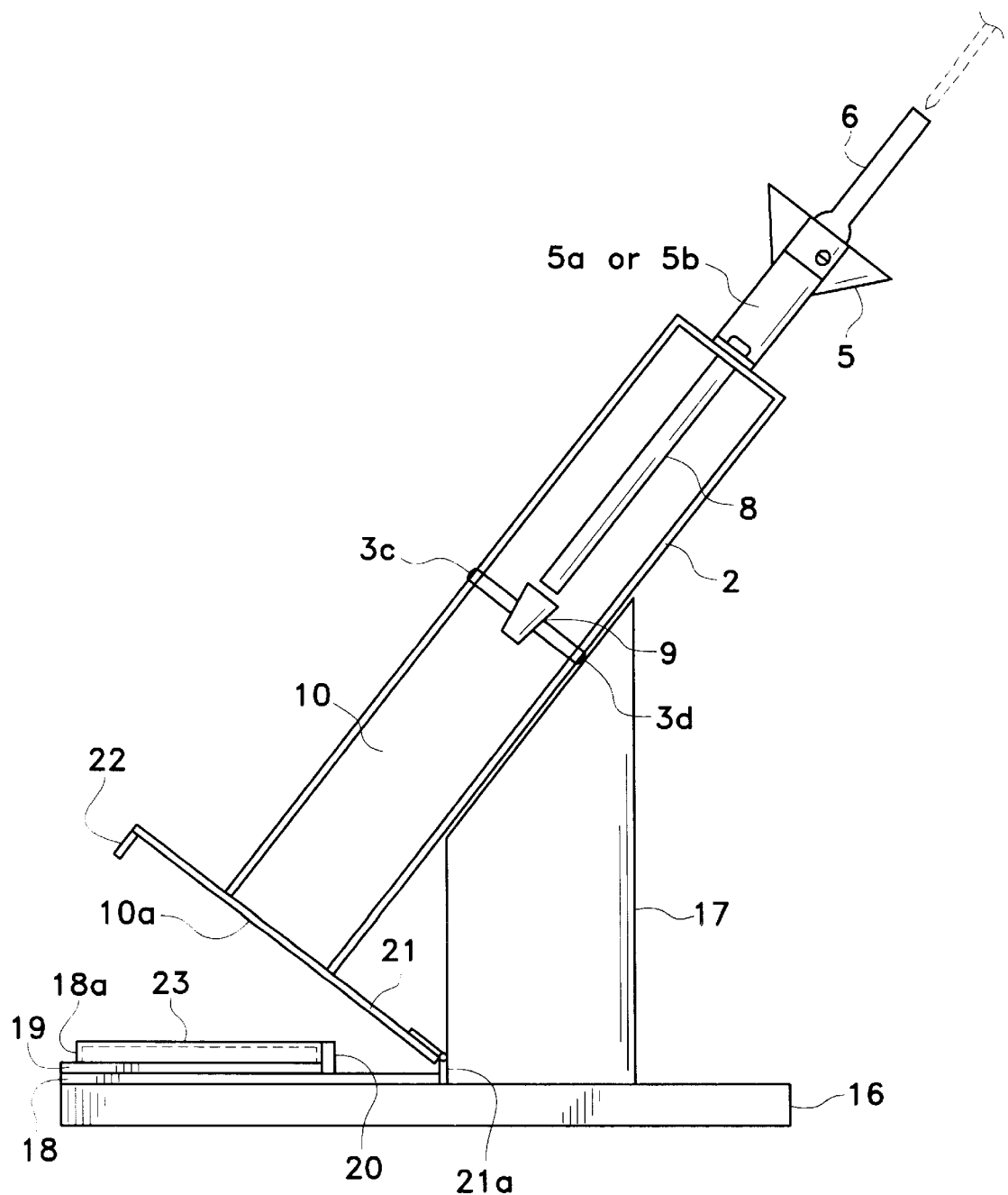
FIG. 4 shows the side view of the device.

As shown in FIGS. 2 and 4, the bottom portion 4 of the frame 2 includes a mounting frame 16 including a backrest 17, a stationary base plate 18 including guide rails 18a is positioned above the mounting frame 16 with a compression pad 19 placed thereupon. The compression pad 19 is positioned against a stop 20. The bottom portion 4 also includes a hinged base plate 21 having a base stop 22 which allows the device 1 to be angled away from the mounting frame 16 during placement and removal of a rearing unit 23 which will be described in detail hereinbelow.

Figure 3:
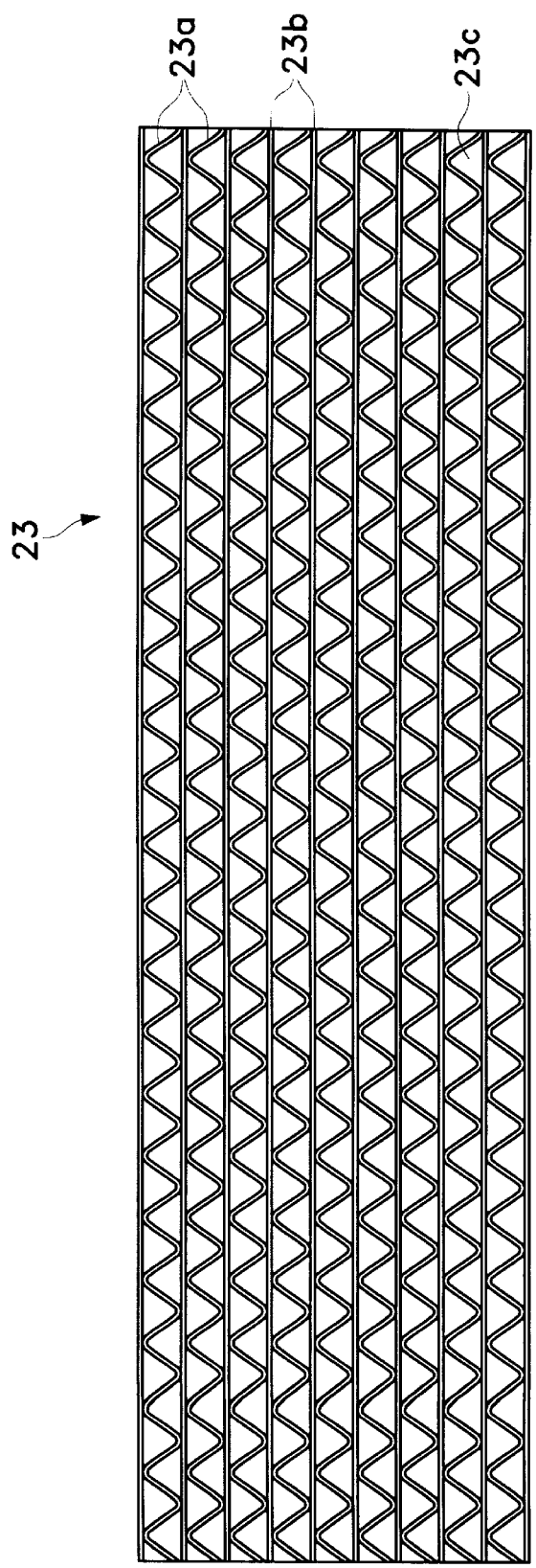
FIG. 3 shows the top view of a rearing unit.

As shown in FIG. 3, the rearing unit 23 is made up of a plurality of individual cells C formed by joining together alternating rows of wave-like or curved walls 23a and straight walls 23b. The bottom of the rearing unit 23 is enclosed by a holding barrier 23c which acts to hold the particulate matter within each cell C. Each rearing unit 23 is generally made up of 500 cells.

As shown in FIG. 4, prior to use, the frame 2 including hinged base plate 21 is tilted backwardly to an open or first position, until the device 1 rests against backrest 17. One of the rearing units 23 is then placed upon the compression pad 19 within the guide rails 18a and against stop 20, which positions the rearing unit 23 directly below and in line with the distribution chamber 10 and the chamber opening 10a. Once in position, the device is moved back to its closed or second position whereupon the rearing unit 23 becomes sandwiched between the hinged base plate 21 and the stationary base plate 18, thus compressing the rearing unit 23 upon the compression pad 19, and rendering the rearing unit 23 stationary during the loading operation. The insert tube 12 is removed and a premeasured portion of eggs and food supply is then poured into the funnel 5. The eggs and food supply travel via gravity flow through the drop tube 8 and fall into the reservoir 9. The insert tube 12 is reinstalled, with the stop 13 contacting the top of the tube guide 6, such that tip 12a is positioned in line with the top of the reservoir 9. Fluid is delivered to tube insert 12 via the fluid source 14. The fluid source pressure generally ranges between 27 and 33 psi. An operator then presses the push button 15a of valve 15 in a quick on/off motion, such that the fluid is delivered in a "puff" or short burst. When the fluid reaches the reservoir 9, the eggs and food stored therein is pushed out into the distribution chamber 10 and out through the chamber opening 10a and delivered evenly over the cells C of the rearing unit 23. The tube insert 12 is then removed and the device 1 tilted backwardly to its open position to remove the filled rearing unit 23. Another rearing unit 23 may then be placed as described hereinabove, such that the filling process may be repeated.

In this manner, the rearing unit 23 is rapidly filled. This device and method allows the rearing unit 23 to be filled at a rate of 5 seconds per unit, thereby affording a viable and quick process for commercial growers of insects (e.g., lacewings) to provide insect eggs and eventually adult insects to the agricultural community.

Thus, in view of the above, the present invention concerns (in part) the following:

A device for rapidly loading small particulate matter, comprising:

a frame having a top and a bottom portion wherein the top portion comprises first and second brackets so as to attach a funnel to said top portion;

said funnel having a top end and an apertured bottom end, said top end constructed so as to house a tube guide, said tube guide being attached to the top end of said funnel through a support bracket;

said funnel further constructed so as to attach to a drop tube at said bottom end, such that said drop tube extends downwardly to a height directly above and centrally positioned with respect to a reservoir, said reservoir further constructed so as to hold a quantity of small particulate matter;

said reservoir constructed so as to be affixed to said frame through brackets, said funnel further constructed so as to deliver said small particulate matter to said reservoir through said drop tube;

a fluid delivery system comprising a movable insert tube having a tip, said system constructed so as to deliver a fluid through said insert tube inserted through said tube guide, said funnel, and said drop tube to a position directly above and centrally positioned with respect to said reservoir, said reservoir holding said small particulate matter, said fluid delivered at a controlled rate;

said bottom portion of said frame comprising a mounting frame including a backrest, a stationary base plate having guide rails constructed to be positioned upon said mounting frame, a compression pad constructed to be positioned upon said stationary base plate, said compression pad further constructed so as to be positioned against a stop;

said bottom portion further comprising a hinged base plate having a base stop, said hinged base plate constructed so as to allow said device to be angled away from said mounting frame during placement and removal of a rearing unit;

said rearing unit further comprising a plurality of holding cells, each of said cells constructed so as to hold said small particulate matter being dispensed from said reservoir.

A method for rapidly loading small particulate matter using the device above, comprising:

(a) tilting said device backwardly to a first position;
(b) placing a rearing unit on a compression pad within guide rails and stop of said device and positioning the rearing unit directly below and in line with a distribution chamber and a chamber opening of the device;
(c) moving the device to its second position and sandwiching the rearing unit between a hinged base plate and a stationary base plate thereby compressing the rearing unit and the compression pad and rendering said rearing unit and compression pad stationary during the loading operation;
(d) removing an insert tube of said device and pouring a premeasured portion of said small particulate matter into a funnel of the device;
(e) moving said small particulate matter via gravity flow through a drop tube into a reservoir of the device;
(f) reinstalling said tube insert over said funnel and contacting a stop of said tube insert with a top portion of a top of a tube guide and positioning a tip of said tube insert in line with a top portion of said reservoir;
(g) connecting a fluid source to said insert tube;
(h) delivering a fluid from said fluid source to said tube insert and delivering a short burst of fluid to said reservoir to push the small particulate matter from said reservoir into a distribution chamber, through a chamber opening and evenly delivering said small particulate matter over a plurality of cells of the rearing unit; and
(i) removing said tube insert and tilting said device to said first position, removing said filled rearing unit and repeating the steps (a)–(h) hereinabove.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A device for rapidly loading small particulate matter, comprising:

a frame having a top and a bottom portion wherein the top portion comprises first and second brackets so as to attach a funnel to said top portion;

said funnel having a top end and an apertured bottom end, said top end constructed so as to house a tube guide, said tube guide being attached to the top end of said funnel through a support bracket;

said funnel further constructed so as to attach to a drop tube at said bottom end, such that said drop tube extends downwardly to a height directly above and centrally positioned with respect to a reservoir, said reservoir further constructed so as to hold a quantity of small particulate matter;

said reservoir constructed so as to be affixed to said frame through brackets, said funnel further constructed so as to deliver said small particulate matter to said reservoir through said drop tube;

a fluid delivery system comprising a movable insert tube having a tip, said system constructed so as to deliver a fluid through said insert tube inserted through said tube guide, said funnel, and said drop tube to a position directly above and centrally positioned with respect to said reservoir, said reservoir holding said small particulate matter, said fluid delivered at a controlled rate;

said bottom portion of said frame comprising a mounting frame including a backrest, a stationary base plate having guide rails constructed to be positioned upon said mounting frame, a compression pad constructed to be positioned upon said stationary base plate, said compression pad further constructed so as to be positioned against a stop;

said bottom portion further comprising a hinged base plate having a base stop, said hinged base plate constructed so as to allow said device to be angled away from said mounting frame during placement and removal of a rearing unit;

said rearing unit further comprising a plurality of holding cells, each of said cells constructed so as to hold said small particulate matter being dispensed from said reservoir.

2. The device according to claim 1, wherein said small particulate matter comprises a mixture of food matter and insect eggs.

3. The device according to claim 1, wherein said fluid comprises air.

4. A method for rapidly loading small particulate matter using the device according to claim 1, comprising:

(a) tilting said device backwardly to a first position;

(b) placing a rearing unit on a compression pad within guide rails and stop of said device and positioning the rearing unit directly below and in line with a distribution chamber and a chamber opening of the device;

(c) moving the device to its second position and sandwiching the rearing unit between a hinged base plate and a stationary base plate thereby compressing the rearing unit and the compression pad and rendering said rearing unit and compression pad stationary during the loading operation;

(d) removing an insert tube of said device and pouring a premeasured portion of said small particulate matter into a funnel of the device;

(e) moving said small particulate matter via gravity flow through a drop tube into a reservoir of the device;

(f) reinstalling said tube insert over said funnel and contacting a stop of said tube insert with a top portion of a top of a tube guide and positioning a tip of said tube insert in line with a top portion of said reservoir;

(g) connecting a fluid source to said insert tube;

(h) delivering a fluid from said fluid source to said tube insert and delivering a short burst of fluid to said reservoir to push the small particulate matter from said reservoir into a distribution chamber, through a chamber opening and evenly delivering said small particulate matter over a plurality of cells of the rearing unit; and (i) removing said tube insert and tilting said device to said first position, removing said filled rearing unit and repeating the steps (a)–(h) hereinabove.

5. The method according to claim 4, wherein said small particulate matter comprises a mixture of food matter and insect eggs.

6. The method according to claim 5, wherein said fluid comprises air.

* * * * *